United States Patent [19]

Masaki et al.

[11] Patent Number: 4,644,063
[45] Date of Patent: Feb. 17, 1987

[54] 1,3-OXAZOLIDINE-2-ONE DERIVATIVES

[75] Inventors: Mituo Masaki, Chiba; Haruhiko Shinozaki, Omiya; Masaru Satoh, Koshigaya; Naoya Moritoh, Kuki; Koichi Hashimoto; Toshiro Kamishiro, both of Misato, all of Japan

[73] Assignee: Nippon Chemiphar Co., Ltd., Tokyo, Japan

[21] Appl. No.: 739,059

[22] Filed: May 29, 1985

[30] Foreign Application Priority Data

Sep. 28, 1984 [JP] Japan .................................. 59-203624

[51] Int. Cl.$^4$ ............................................. C07D 413/06
[52] U.S. Cl. ..................... 546/209; 548/229; 548/232
[58] Field of Search ................. 546/209; 548/229, 232

[56] References Cited

U.S. PATENT DOCUMENTS 2,437,389  3/1946  Homeyer ............................ 548/229
3,131,197  4/1964  Swintosky .......................... 548/232
3,687,965  8/1972  Fauran et al. ..................... 546/209

OTHER PUBLICATIONS

Chemical Abstracts, vol. 62, (1965), (Abstracting Zikolova et al. in "Farmatsiya", (Sofia) vol. 14, No. 5, pp. 16-21) (1964).

Primary Examiner—Robert T. Bond
Attorney, Agent, or Firm—Oblon, Fisher, Spivak, McClelland & Maier

[57] ABSTRACT

1,3-Oxazolidine-one derivatives of the following formula

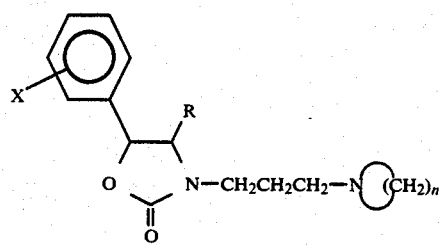

where R is straight or branched alkyl of $C_3$–$C_8$, X is hydrogen, halogen, lower alkyl or lower alkoxy and n is 4, 5 or 6, or their acid addition salts are effective for medicinal and agricultural use.

4 Claims, No Drawings

1,3-OXAZOLIDINE-2-ONE DERIVATIVES

BACKGROUND OF THE INVENTION

1. Field of the Invention

This invention relates to novel 1,3-oxazolidine-2-one derivatives and more specifically to 1,3-oxazolidine-2-one derivatives each represented by the general formula (I):

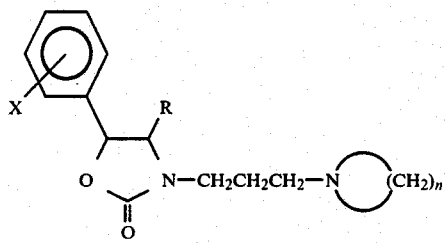

wherein R is a straight or branched alkyl group having 3 to 8 carbon atoms, X is a hydrogen or halogen atom or a lower alkyl or lower alkoxy group and n is an integer of 4 to 6, or acid addition salts thereof. Further, the invention relates to processes for the preparation of such derivatives.

2. Prior Art

It has been emphatically suggested that glutamic acid acts as an excitatory neurotransmitter at the central nervous systems of higher animals and at the neuromuscular junctions of lower animals ["Glutamate as a Neurotransmitter" edited by G. D. Chiara & G. L. Gessa, Raven Press, New York, 1981 and H. M. Gerschenfeld: Physiol. Rev., 53, 1-119 (1973)]. It has also been reported that dystropy, rigidity, tremor, convulsion and the like are induced from administration of kainic acid, domoic acid, quisqualic acid, ibotenic acid or the like, which acid is an extremely strong agonist for glutamic acid in higher animals [Oleny et al: Brain Res., 77, 507-512 (1974)].

It has also been known that as aging proceeds, the central and peripheral nervous systems undergo hypoergia to develop Parkinson's disease, mctoneuron disorders, dementia, tremor, spinocerebellar degeneracy the like. These diseases are considered to be attributable to off-balanced equilibration between excitatory nerves and inhibitory nerves (for example, the equilibration between glutamic acid and GABA) due to loss of neurons at certain specific sites or overall hypoergia of the nervous systems [Toshishige Hirai: Shinkei Shimpo, 17, 69 (1973)].

With the foregoing in view, medicines that can selectively block glutamic acid are useful for the therapy of neuropathy from which the senility would most often suffer and which would involve such complaints as vertigo, shoulder discomfort, convulsion, tremor and the like, all of them resulting from off-balanced nervous systems or hyperstenia in muscle discharge.

Glutamic aicd acts as an excitatory neurotransmitter for neuromuscular junctions of insects. Chemicals capable of blocking glutamic acid are also suitable for agricultural use for their ability to reduce and weaken insects' activities [Morifusa Eto: Kagaku to Seibutsu, 21, 725 (1983)].

Through intensive research leading to the invention, it has been found that 1,3-oxazolidine-2-one derivatives of the formula (I) above have excellent blocking effects against glutamic acid as well as neuraxial muscle relaxing effects, i.e. rigidity reducing and releasing effects on anemic decerabrate rigidity samples.

As compounds structurally similar to the compounds of the invention, there have previously been known 4-methyl-5-phenyl-3-(2-piperidinoethyl)-1,3-oxazolidine-2-one [Zikolova et al: Farmatsiya (Sofia), 14, 16-21 (1964) and Nikolova: Izv. Inst. Fiziol., Bulg. Akad. Nauk., 12, 217-226 (1969)] and 4-methyl-5-phenyl-3-(2-pyrrolidinoethyl)-1,3-oxazolidine-2-one [Zikolova et al: Farmatsiya (Sofia), 14, 16-21 (1964)].

However, Zikolova et al does not report anything about the pharmacological effects of these compounds. Nikolova reports that 4-methyl-5-phenyl-3-(2-piperidinoethyl)-1,3-oxazolidine-2-one has an analgesic effect, but exerts no anti-convulsion nor neuraxial muscle relaxing effects. In an experiment conducted by the inventors of this invention, the latter compound has been found to be extremely weak in its neuraxial muscle relaxing effect.

SUMMARY OF THE INVENTION

An object of the invention is therefore to provide novel 1,3-oxazolidine-2-one derivatives which are represented by the formula (I) above and which have excellent blocking effects against glutamic acid and rigidity reducing and releasing effects and hence are useful as both medicines and agricultural chemicals.

Another object of the invention is to provide novel processes suitable for use in the preparation of such 1,3-oxazolidine-2-one derivatives.

This invention provides, in a first aspect, a 1,3-oxazolidine-2-one derivative represented by the following formula:

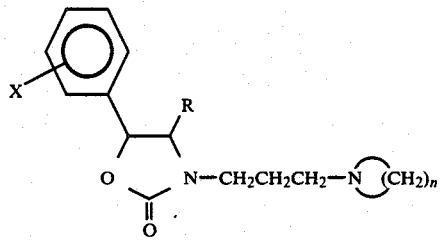

wherein R is a straight or branched alkyl group having 3 to 8 carbon atoms, X is a hydrogen or halogen atom or a lower alkyl or lower alkoxy group and n is an integer of 4 to 6, or an acid addition salt thereof.

In a second aspect the invention provides a process for preparing such derivative or its acid addition salt, which comprises reacting a compound represented by the following formula:

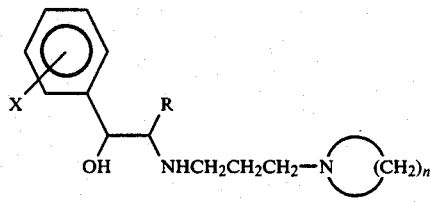

wherein R, X and n are as defined above, with a dialkyl carbonate or a compound represented by the following formula:

wherein Y is a halogen atom or a trichloromethyloxy group; and optionally converting the reaction product into an acid addition salt thereof.

In a third aspect the invention provides a process for preparing such derivative or its acid addition salt, which comprises reacting a compound represented by the following formula:

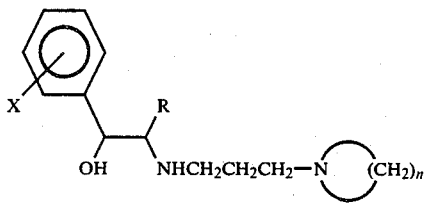

wherein R, X and n are as defined above, wih a compound represented by the following formula:

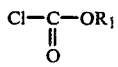

wherein $R_1$ is a lower alkyl group to form a compound represented by the following formula:

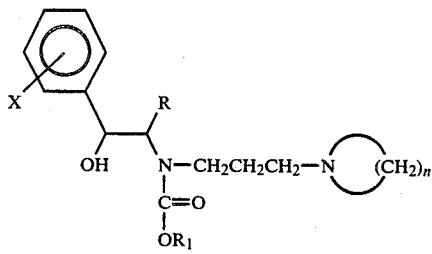

wherein R, $R_1$, X and n are as defined above; heating the last-mentioned compound in the presence of a base to cyclize the same; and optionally converting the reaction product into an acid addition salt thereof.

In a fourth aspect the invention provides a process for preparing such derivative or its acid addition salt, which comprises reacting, in the presence of potassium carbonate or sodium carbonate, a compound represented by the following formula:

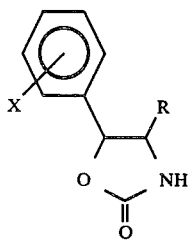

wherein R and X are as defined above, with a compound represented by the following formula:

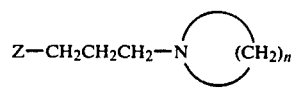

wherein Z is a halogen atom or a tosyloxy, mesyloxy or acetoxy group and n is as defined above; and optionally converting the reaction product into an acid addition salt thereof.

DETAILED DESCRIPTION OF THE INVENTION

Compounds of this invention have the formula (I) referred to above. Straight or branched alkyl groups useful as R in the formula (I) include for example propyl, butyl, pentyl, hexyl, heptyl, octyl, 1-methylethyl, 1-methylpropyl, 2-methylpropyl, 1-methylbutyl, 2-methylbutyl, 3-methylbutyl, 1-methylpentyl, 4-methylpentyl, 1-methylhexyl, 5-methylhexyl, 1-methylheptyl, 6-methylheptyl, 1,1-dimethylpropyl, 1-ethylbutyl and the like. Lower alkyl groups useful as X include for example methyl, ethyl, n-propyl and isopropyl. Lower alkoxy groups also useful as X include for example methoxy, ethoxy and n-propyloxy. Halogen atoms also useful as X include for example chlorine, bromine and fluorine.

Each of the compounds contemplated by the invention includes its stereoscopic isomers, i.e. a cis-isomer (4RS,5SR) and a trans-isomer (4RS,5RS), and its optical isomers (4R,5S), (4S,5R), (4R,5R) and (4S,5S). It is to be noted that these two types of isomers are inside the scope of the invention.

The compounds of this invention can be prepared for example by either one of the following processes. Process 1:

A compound of the formula (II) is reacted with a compound of the formula (III) to prepare the desired compound of the formula (I).

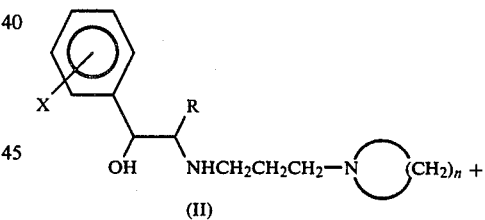

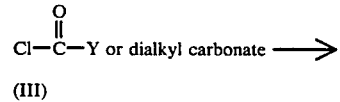

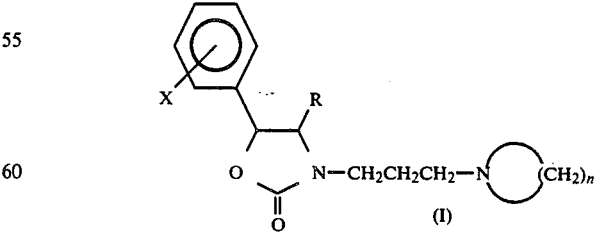

wherein Y is a halogen atom or a trichloromethyloxy group and R, X and n are as defined with respect to the formula (I) above.

The reaction is effected in the presence of an alkali such as sodium hydroxide and in a heterogeneous solvent of water and an organic solvent such as ether or chloroform at a temperature of −10° to +10° C. It is preferred that a dialkyl carbonate or the compound (III) be used in the range of 2 to 4 moles per mole of the compound (II) and that reaction time be in the range of 0.5 to 2 hours. Process 2:

The compound (II) is reacted with a compound of the formula (IV) to form a compound of the formula (V) which is then heated in the presence of a base to cyclize the same into the compound (I).

same in the presence of a base such as sodium methoxide, sodium ethoxide or aluminum isopropoxide and in a solvent such as toluene or xylene and at a temperature of 100° to 140° C.

It is preferred that the compound (IV) be used in the range of 1 to 2 moles per mole of the compound (II) and that reaction time be in the range of 0.5 to 2 hours.

Process 3:

A compound of the formula (VI) is reacted with a compound of the formula (VII) to prepare the compound (I).

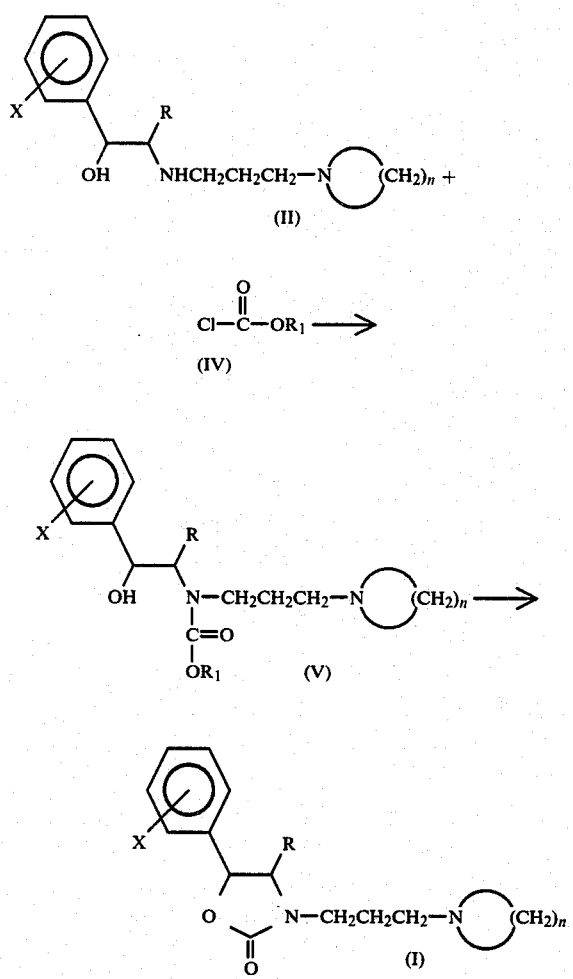

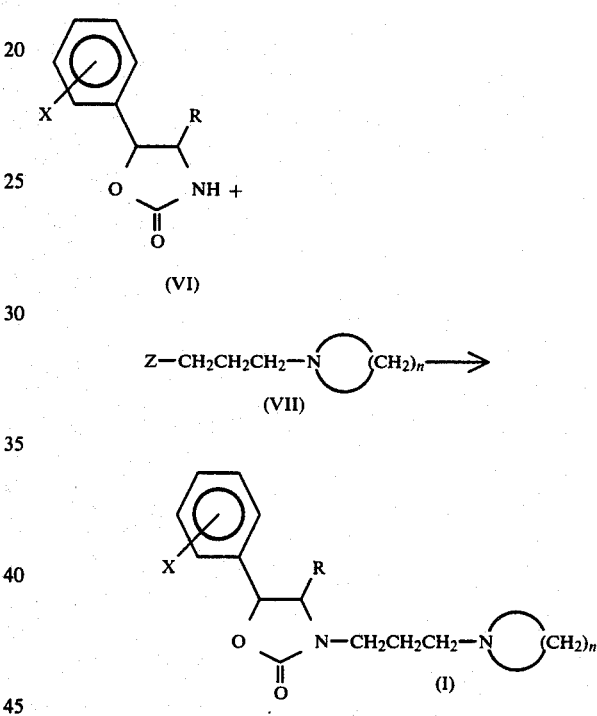

wherein $R_1$ is a lower alkyl group and R, X and n are as defined above.

The reaction of the compound (II) with the compound (IV) is effected in the presence of an alkali such as sodium hydroxide and in a heterogeneous solvent of water and an organic solvent such as ether or chloroform at a temperature of −5° to +15° C. The cyclization of the compound (V) is effected by heating the wherein Z is a halogen atom or a tosyloxy, mesyloxy or acetoxy group and R, X and n are as defined above.

The reaction of the compound (VI) with the compound (VII) is effected in the presence of a mild base such as potassium carbonate or sodium carbonate and in an organic solvent such as acetone, methyl ethyl ketone or methyl isobutyl ketone and at a temperature of 50° C. to the reflux temperature. It is preferred that the compound (VII) and the mild base be used, respectively, in the range of 1 to 2 times and at least 2 times the mole of the compound (VI) and that reaction time be in the range of 2 to 50 hours. the compound (VII) is preferably used as hydrochloride which is stable.

The compounds (II) and (VI), both starting materials for the practice of processes 1 to 3 above, can be prepared for example by the following reaction scheme.

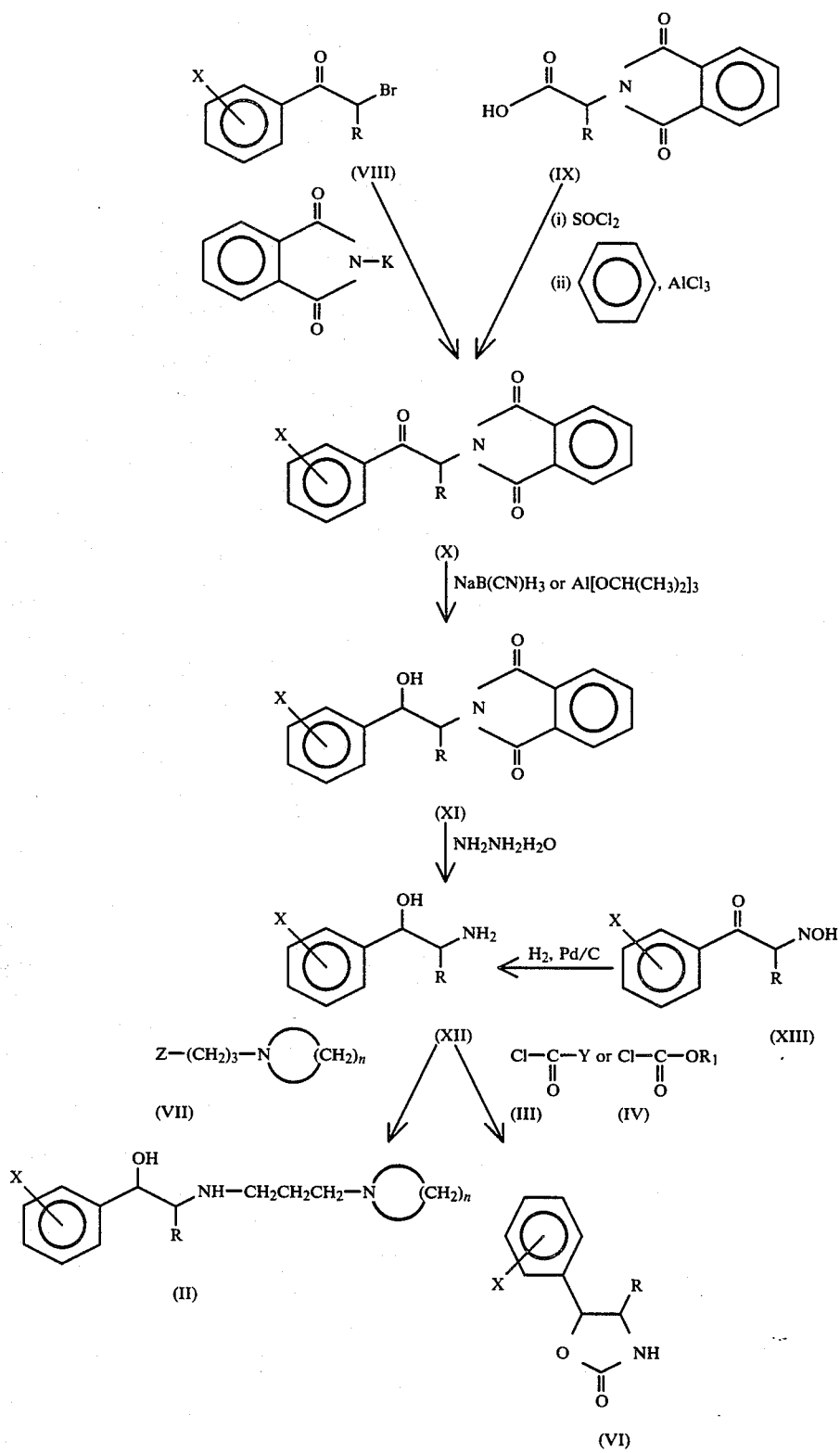

wherein R, $R_1$, X, Y, Z and n are as defined above.

A compound of the formula (X) can be prepared by reaction of a compound of the formula (VIII) with potassium phthalimide or by Friedel-Crafts acylation of acid chloride and benzene in the presence of an aluminum chloride catalyst. The acid chloride is derived from a compound of the formula (IX) by treatment with thionyl chloride.

A compound of the formula (XI) can be prepared by reduction of the compound (X) with a reducing agent such as sodium cyanoborohydride or aluminum isopropoxide.

A compound of the formula (XII) can be obtained by hydrazinolysis of the compound (XI) or by palladium-catalyzed hydrogenation of a compound of the formula (XIII).

The compound (II) can be obtained by reaction of the compound (XII) with the compound (VII). The compound (VI) can be prepared by reaction of the compound (XII) with the compound (III) or (IV).

Either isomer of the compound (I) is obtainable either by a method which can predominantly produce one isomer or by separation of a mixture of isomers of the compound (XI).

The 1,3-oxazolidine-2-one derivatives (I) thus prepared can be converted in conventional manner to their acid addition salts. Acid addition salts useful in the invention include for example hydrochloride, hydrobromide, sulfate, p-toluene-sulfonate, fumarate, citrate, maleate, oxalate and the like.

The following compounds are particularly typical of the compounds (I) of the invention.

Compound 1: (4RS,5SR)-4-(1-methylethyl)-5-phenyl-3-(3-piperidinopropyl)-1,3-oxazolidine-2-one
Compound 2: (4RS,5RS)-4-(1-methylethyl)-5-phenyl-3-(3-piperidinopropyl)-1,3-oxazolidine-2-one
Compound 3: (4RS,5SR)-4-(2-methylpropyl)-5-phenyl-3-(3-piperidinopropyl)-1,3-oxazolidine-2-one
Compound 4: (4RS,5RS)-4-(2-methylpropyl)-5-phenyl-3-(3-piperidinopropyl)-1,3-oxazolidine-2-one
Compound 5: (4S,5R)-4-(2-methylpropyl)-5-phenyl-3-(3-piperidinopropyl)-1,3-oxazolidine-2-one
Compound 6: (4R,5S)-4-(2-methylpropyl)-5-phenyl-3-(3-piperidinopropyl)-1,3-oxazolidine-2-one
Compound 7: (4S,5S)-4-(2-methylpropyl)-5-phenyl-3-(3-piperidinopropyl)-1,3-oxazolidine-2-one
Compound 8: (4R,5R)-4-(2-methylpropyl)-5-phenyl-3-(3-piperidinopropyl)-1,3-oxazolidine-2-one
Compound 9: (4RS,5SR)-4-(1-methylethyl)-5-phenyl-3-(3-pyrrolidinopropyl)-1,3-oxazolidine-2-one
Compound 10: (4RS, 5RS)-4-(1-methylethyl)-5-phenyl-3-(3-pyrrolidinopropyl)-1,3-oxazolidine-2-one
Compound 11: (4RS,5SR)-4-(1-methylethyl)-3-[3-(perhydroazepine-1-yl)propyl]-5-phenyl-1,3-oxazolidine-2-one
Compound 12: (4RS,5RS)-4-(1-methylethyl)-3-[3-(perhydroazepine-1-yl)propyl]-5-phenyl-1,3-oxazolidine-2-one
Compound 13: (4RS,5SR)-4-(2-methylpropyl)-5-phenyl-3-(3-pyrrolidinopropyl)-1,3-oxazolidine-2-one
Compound 14: (4RS,5RS)-4-(2-methylpropyl)-5-phenyl-3-(3-pyrrolidinopropyl)-1,3-oxazolidine-2-one
Compound 15: (4RS,5SR)-4-(2-methylpropyl)-3-[3-(perhydroazepine-1-yl-)propyl]-5-phenyl-1,3-oxazolidine-2-one
Compound 16: (4RS,5RS)-4-(2-methylpropyl)-3-[3-(perhydroazepine-1-yl-)propyl]-5-phenyl-1,3-oxazolidine-2-one
Compound 17: (4S,5R)-4-(2-methylpropyl)-3-[3-(perhydroazepine-1-yl-)propyl]-5-phenyl-1,3-oxazolidine-2-one
Compound 18: (4R,5S)-4-(2-methylpropyl)-3-[3-(perhydroazepine-1-yl-)propyl]-5-phenyl-1,3-oxazolidine-2-one
Compound 19: (4S,5S)-4-(2-methylpropyl)-3-[3-(perhydroazepine-1-yl-)propyl]-5-phenyl-1,3-oxazolidine-2-one
Compound 20: (4R,5R)-4-(2-methylpropyl)-3-[3-(perhydroazepine-1-yl-)propyl]-5-phenyl-1,3-oxazolidine-2-one
Compound 21: (4RS,5SR)-5-(2-methylphenyl)-4-(2-methylpropyl)-3-(3-piperidinopropyl)-1,3-oxazolidine-2-one
Compound 22: (4RS,5RS)-5-(2-methylphenyl)-4-(2-methylpropyl)-3-(3-piperidinopropyl)-1,3-oxazolidine-2-one
Compound 23: (4RS,5SR)-5-(3-methylphenyl)-4-(2-methylpropyl)-3-(3-piperidinopropyl)-1,3-oxazolidine-2-one
Compound 24: (4RS,5RS)-5-(3-methylphenyl)-4-(2-methylpropyl)-3-(3-piperidinopropyl)-1,3-oxazolidine-2-one
Compound 25: (4RS,5SR)-5-(4-methylphenyl)-4-(2-methylpropyl)-3-(3-piperidinopropyl)-1,3-oxazolidine-2-one
Compound 26: (4RS,5RS)-5-(4-methylphenyl)-4-(2-methylpropyl)-3-(3-piperidinopropyl)-1,3-oxazolidine-2-one
Compound 27: (4RS,5SR)-5-(4-methoxyphenyl)-4-(2-methylpropyl)-3-(3-piperidinopropyl)-1,3-oxazolidine-2-one
Compound 28: (4RS,5RS)-5-(4-methoxyphenyl)-4-(2-methylpropyl)-3-(3-piperidinopropyl)-1,3-oxazolidine-2-one
Compound 29: (4RS,5SR)-5-(4-fluorophenyl)-4-(2-methylpropyl)-3-(3-piperidinopropyl)-1,3-oxazolidine-2-one
Compound 30: (4RS,5RS)-5-(4-fluorophenyl)-4-(2-methylpropyl)-3-(3-piperidinopropyl)-1,3-oxazolidine-2-one
Compound 31: (4RS,5SR)-5-(4-chlorophenyl)-4-(2-methylpropyl)-3-(3-piperidinopropyl)-1,3-oxazolidine-2-one
Compound 32: (4RS,5RS)-5-(4-chlorophenyl)-4-(2-methylpropyl)-3-(3-piperidinopropyl)-1,3-oxazolidine-2-one
Compound 33: (4RS,5RS)-5-phenyl-3-(3-piperidinopropyl)-4-propyl-1,3-oxazolidine-2-one
Compound 34: (4RS,5SR)-5-phenyl-3-(3-piperidinopropyl)-4-propyl-1,3-oxazolidine-2-one
Compound 35: (4RS,5RS)-4-butyl-5-phenyl-3-(3-piperidinopropyl)-1,3-oxazolidine-2-one
Compound 36: (4RS,5SR)-4-butyl-5-phenyl-3-(3-piperidinopropyl)-1,3-oxazolidine-2-one
Compound 37: (4RS,5RS)-4-pentyl-5-phenyl-3-(3-piperidinopropyl)-1,3-oxazolidine-2-one
Compound 38: (4RS,5SR)-4-pentyl-5-phenyl-3-(3-piperidinopropyl)-1,3-oxazolidine-2-one
Compound 39: (4RS,5RS)-4-(3-methylbutyl)-5-phenyl-3-(3-piperidinopropyl)-1,3-oxazolidine-2-one
Compound 40: (4RS,5SR)-4-(3-methylbutyl)-5-phenyl-3-(3-piperidinopropyl)-1,3-oxazolidine-2-one
Compound 41: (4RS,5RS)-4-hexyl-5-phenyl-3-(3-piperidinopropyl)-1,3-oxazolidine-2-one
Compound 42: (4RS,5SR)-4-hexyl-5-phenyl-3-(3-piperidinopropyl)-1,3-oxazolidine-2-one
Compound 43: (4RS,5RS)-4-hexyl-5-phenyl-3-(3-pyrrolidinopropyl)-1,3-oxazolidine-2-one
Compound 44: (4RS,5SR)-4-hexyl-5-phenyl-3-(3-pyrrolidinopropyl)-1,3-oxazolidine-2-one
Compound 45: (4RS,5RS)-4-hexyl-3-[3-(perhydroazepine-1-yl)propyl]-5-phenyl-1,3-oxazolidine-2-one
Compound 46: (4RS,5SR)-4-hexyl-3-[3-(perhydroazepine-1-yl)propyl]-5-phenyl-1,3-oxazolidine-2-one
Compound 47: (4R,5R)-4-hexyl-5-phenyl-3-(3-piperidinopropyl)-1,3-oxazolidine-2-one
Compound 48: (4R,5S)-4-hexyl-5-phenyl-3-(3-piperidinopropyl)-1,3-oxazolidine-2-one Compound 49: (4S,5S)-4-hexyl-5-phenyl-3-(3-piperidinopropyl)-1,3-oxazolidine-2-one
Compound 50: (4S,5R)-4-hexyl-5-phenyl-3-(3-piperidinopropyl)-1,3-oxazolidine-2-one
Compound 51: (4RS,5RS)-4-heptyl-5-phenyl-3-(3-piperidinopropyl)-1,3-oxazolidine-2-one
Compound 52: (4RS,5SR)-4-heptyl-5-phenyl-3-(3-piperidinopropyl)-1,3-oxazolidine-2-one
Compound 53: (4RS,5RS)-5-phenyl-3-(3-piperidinopropyl)-4-octyl-1,3-oxazolidine-2-one
Compound 54: (4RS,5SR)-5-phenyl-3-(3-piperidinopropyl)-4-octyl-1,3-oxazolidine-2-one
Compound 55: (4RS,5RS)-4-(1-methylbutyl)-5-phenyl-3-(3-piperidinopropyl)-1,3-oxazolidine-2-one
Compound 56: (4RS,5SR)-4-(1-methylbutyl)-5-phenyl-3-(3-piperidinopropyl)-1,3-oxazolidine-2-one
Compound 57: (4RS,5RS)-4-(4-methylpentyl)-5-phenyl-3-(3-piperidinopropyl)-1,3-oxazolidine-2-one
Compound 58: (4RS,5SR)-4-(4-methylpentyl)-5-phenyl-3-(3-piperidinopropyl)-1,3-oxazolidine-2-one
Compound 59: (4RS,5RS)-4-(1-methylpentyl)-5-phenyl-3-(3-piperidinopropyl)-1,3-oxazolidine-2-one
Compound 60: (4RS,5SR)-4-(1-methylpentyl)-5-phenyl-3-(3-piperidinopropyl)-1,3-oxazolidine-2-one
Compound 61: (4RS,5RS)-4-(5-methylhexyl)-5-phenyl-3-(3-piperidinopropyl)-1,3-oxazolidine-2-one
Compound 62: (4RS,5SR)-4-(5-methylhexyl)-5-phenyl-3-(3-piperidinopropyl)-1,3-oxazolidine-2-one
Compound 63: (4RS,5RS)-4-(1-methylhexyl)-5-phenyl-3-(3-piperidinopropyl)-1,3-oxazolidine-2-one
Compound 64: (4RS,5SR)-4-(1-methylhexyl)-5-phenyl-3-(3-piperidinopropyl)-1,3-oxazolidine-2-one
Compound 65: (4RS,5RS)-4-(6-methylheptyl)-5-phenyl-3-(3-piperidinopropyl)-1,3-oxazolidine-2-one
Compound 66: (4RS,5SR)-4-(6-methylheptyl)-5-phenyl-3-(3-piperidinopropyl)-1,3-oxazolidine-2-one
Compound 67: (4RS,5RS)-4-(1-methylheptyl)-5-phenyl-3-(3-piperidinopropyl)-1,3-oxazolidine-2-one
Compound 68: (4RS,5SR)-4-(1-methylheptyl)-5-phenyl-3-(3-piperidinopropyl)-1,3-oxazolidine-2-one
Compound 69: (4RS,5RS)-4-(1,1-dimethylpropyl)-5-phenyl-3-(3-piperidinopropyl)-1,3-oxazolidine-2-one
Compound 70: (4RS,5SR)-4-(1,1-dimethylpropyl)-5-phenyl-3-(3-piperidinopropyl)-1,3-oxazolidine-2-one
Compound 71: (4RS,5RS)-4-(1-ethylbutyl)-5-phenyl-3-(3-piperidinopropyl)-1,3-oxazolidine-2-one
Compound 72: (4RS,5SR)-4-(1-ethylbutyl)-5-phenyl-3-(3-piperidinopropyl)-1,3-oxazolidine-2-one The effectiveness of the compounds (I) according to this invention was determined with respect to the blocking effects against glutamic acid, the neuraxial muscle relaxing effects (the rigidity reducing and releasing effects on anemic decerebrate rigidity samples) and the toxicity levels. The following compounds were used for comparative purposes.

Comparative compound 1:
toluperisone hydrochloride
Comparative compound 2:
(4RS,5SR)-4-methyl-5-phenyl-3-(2-piperidinoethyl)-1,3-oxazolidine-2-one hydrochloride
Comparative compound 3:
(4RS,5RS)-4-methyl-5-phenyl-3-(2-piperidinoethyl)-1,3-oxazolidine-2-one hydrochloride
Comparative compound 4:
(4RS,5SR)-4-methyl-5-phenyl-3-(2-pyrrolidinoethyl)-1,3-oxazolidine-2-one hydrochloride
Comparative compound 5:
(4RS,5RS)-4-methyl-5-phenyl-3-(2-pyrrolidinoethyl)-1,3-oxazolidine-2-one hydrochloride

EXPERIMENT 1

Effects on Anemic Decerebrate Rigidity Sample

An anemic decerebrate rigidity sample was prepared principally in accordance with the procedure of Fukuda et al [Japan J. Pharmacol., 24, 810 (1974)]. That is, Wistar male rats (body weight: 270 to 350 g) were held on their backs and incised at their cervices under etherization. A cannulated trachemas was then inserted in the incised cervix of each of the rats to thereby double-ligate and cut its trachea and esophagus and both of its common carotid arteries. Thereafter, its occipital bone was exposed through which a circular hole was bored to double-ligate the centrally extending basilar artery. As the rat started coming out of anesthetization, its front limbs became rigid. Measurement was conducted by recording electromyographic (EMG) response from the muscle of the forelimb (M. triceps brachii) of the rat in the rigid state. The EMG pulses were converted to accumulated values every 10 seconds and recorded as a histogram on a recorder.

The effect of each test compound on the rigidity sample was evaluated in terms of the suppression rate. This rate was calculated first by determining the area of a decreased EMG muscle pulse part on the histogram upon passage of 10 minutes after administration of a physiological saline solution of each test compound (3 mg/kg) through the femoral vein and then in accordance with the following equation.

Suppression rate (%) = $a/A \times 100$ where
a: EMG pulse area decreased as a result of the administration of the test compound; and
A: EMG pulse area when no test compound was administered (control).

The results are shown in Table 1.

TABLE 1

| Test compound | Suppression rate (%) |
|---|---|
| Present compound | |
| 1 | 12.0 |
| 2 | 19.8 |
| 3 | 18.0 |
| 4 | 21.2 |
| 5 | 37.7 |
| 6 | 14.9 |
| 7 | 64.8 |
| 8 | 12.0 |
| 10 | 18.7 |
| 14 | 10.2 |
| 17 | 93.0 |
| 25 | 10.9 |
| 27 | 8.4 |
| 29 | 9.9 |
| Comparative compound | |
| 1 | 4.8 |
| 2 | 3.6 |
| 3 | 2.2 |
| 4 | 1.0 |
| 5 | 3.0 |

EXPERIMENT 2

Blocking effects against Glutamic Acid at Neuromuscular Junctions of Crayfish The method of Ishida et al [J. Physiol., 298, 301–319 (1980)] and that of Shinozaki et al [Comp. Biochem. Physiol., 70c, 49–58 (1981)] were followed. That is, the opener muscles of the first walking legs of crayfish were used as meterials for this experiment. The neurcmuscular sample was held in a bath whereby a physiological solution [composition (mM): NaCl (195), CaCl$_2$ (18), KCl (5.4), tris-maleate buffer (pH 7.5; 10), glucose (11)] for use with the crayfish was perfused at room temperature and at a constant flow rate. Glass micro-electrodes, each of which was filled with a 3M KCl solution, were inserted in a central part of the muscle fiber to intracellularly record changes in the potential of the muscular cell membrane.

The blocking effect of each test compound against glutamic acid was evaluated in terms of the supperssion rate to depolarization which was induced by perfusing and applying L-glutamic acid ($10^{-4}$M) in a 5-minute pretreatment with a solution of the test compound. The results are shown in Table 2.

TABLE 2

| Test compound | Concentration of test compound in solution (M) | Blocking rate against glutamic acid (%) |
|---|---|---|
| Present compound | | |
| 3 | $2 \times 10^{-4}$ | 89 |
| 4 | $2 \times 10^{-4}$ | 88 |
| 5 | $2 \times 10^{-4}$ | 91 |
| 7 | $2 \times 10^{-4}$ | 92 |
| 13 | $2 \times 10^{-4}$ | 80 |
| 17 | $2 \times 10^{-4}$ | 90 |
| 35 | $2 \times 10^{-5}$ | 68 |
| 36 | $2 \times 10^{-5}$ | 53 |
| 37 | $2 \times 10^{-5}$ | 58 |
| 40 | $2 \times 10^{-5}$ | 61 |
| 41 | $2 \times 10^{-5}$ | 69 |
| Comparative compound | | |
| 2 | $2 \times 10^{-4}$ | 0 |
| 4 | $2 \times 10^{-4}$ | 45 |

EXPERIMENT 3

Acute Toxicity

Using ddN male mice, the acute toxicity level of each test compound was determined in accordance with an up-and-down method. Some of the test compounds used were dissolved in physiological saline and administered through the caudal vein. The results are shown in Table 3.

TABLE 3

| Test compound | LD$_{50}$ (mg/kg, iv) |
|---|---|
| Present compound | |
| 1 | 29.7 |
| 2 | 18.8 |
| 3 | 55.5 |
| 4 | 29.9 |
| 5 | 69.0 |
| 7 | 30.4 |
| 10 | 54.6 |
| 13 | 75.1 |
| 14 | 53.2 |
| 17 | 40.1 |
| 25 | 34.9 |
| 27 | 39.8 |
| 29 | 66.1 |

TABLE 3-continued

| Test compound | LD$_{50}$ (mg/kg, iv) |
|---|---|
| 40 | 53.6 |

This invention will now be described by the following specific examples and reference examples.

EXAMPLE 1

(1)

(4RS,5SR)-4-(1-methylethyl)-5-phenyl-3-(3-piperidinopropyl)-1,3-oxazolidine-2-one (1RS,2SR)-3-Methyl-1-phenyl-2-(3-piperidinopropylamino)butane-1-ol dihydrochloride (755 mg, 2.00 mmol) was suspended in a 10% aqueons solution of sodium hydroxide (12 ml), followed by addition of ether (28 ml). The mixture was stirred and, when became clear, ice-cooled. A 20% solution of trichloromethyl chloroformate (hereinafter referred to simply as "TCF") in toluene (4.0 ml) was added dropwise over one hour. After completion of the TCF addition, the mixture was stirred at room temperature for 30 minutes. The organic layer was separated, washed once with brine, dried over sodium sulfate and then evaporated under reduced pressure. The resulting crude product was purified by silica gel column chromatography (silica gel: 7 g, solvent: chloroform/methanol=20/1) to obtain 613 mg of the intended compound as pale yellow crystals (yield: 93%).

IR$\nu_{max}^{KBr}$(cm$^{-1}$): 2930, 2860, 2760, 1730, 1605, 1440, 1415, 1125, 1030, 755, 695.

NMR (CDCl$_3$) δ: 0.68 (3H, d, J=7Hz, CHC$\underline{H}_3$)
0.89 (3H, d, J=7Hz, CHC$\underline{H}_3$)

1.20–2.01 (9H, m, C$\underline{H}$(CH$_3$)$_2$,

2.12–2.52 (6H, m,
)

2.92–3.30 (1H, m, O
NC$\underline{H}$)

3.54–4.00 (2H, m, O NC$\underline{H}$)

5.60 (1H, d, J=8Hz, C$\underline{H}$—O)
7.16–7.48 (5H, m, aromatic protons)

(2)
(4RS,5SR)-4-(1-methylethyl)-5-phenyl-3-(3-piperidinopropyl)-1,3-oxazolidine-2-one fumarate The compound (430 mg, 1.30 mmol) obtained in item (1) of this Example was dissolved in ethanol (4 ml), followed by addition of a hot ethanol solution (5 ml) of fumaric acid (151 mg, 1.30 mmol). The solution was evaporated under reduced pressure and the residue was dissolved in acetone and allowed to stand overnight. After ice-cooling of the mixture, precipitated crystals were collected by filtration. The crystals were washed three times with acetone to obtain 491 mg of the intended compound as white crystals (yield: 85%).

m.p.: 142°–144° C. (decomposed).

IR $\nu_{max}^{KBr}$(cm$^{-1}$): 3440, 2940, 2880, 1740, 1700, 1640, 1560, 1420, 1250, 1200, 980, 750, 700.

NMR (CDCl$_3$:CD$_3$OD = 6:1)δ:
0.65 (3H, d, J = 7Hz, CHC$\underline{H}$$_3$)
0.86 (3H, d, J = 7Hz, CHC$\underline{H}$$_3$)

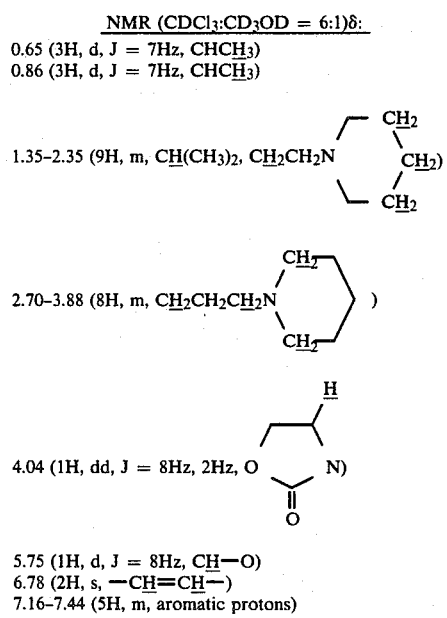

5.75 (1H, d, J = 8Hz, C$\underline{H}$—O)
6.78 (2H, s, —C$\underline{H}$=C$\underline{H}$—)
7.16–7.44 (5H, m, aromatic protons)

EXAMPLE 2
(1)
(1RS,2SR)-2-[N-ethoxycarbonyl-N-(3-piperidinopropyl)amino]-4-methyl-1-phenylpentane-1-ol To a chloroform solution (6 ml) of (1RS,2SR)-4-methyl-1-phenyl-2-(3-piperidonopropylamino)pentane-1-ol (637 mg, 2.00 mmol) was added dropwise with ice-cooling and stirring about one half of a chloroform solution (4 ml) of ethyl chlorocarbonate (543 mg, 5.0 mmol) while controlling the reaction temperature below 15° C. Thereafter, the remaining half portion of the chloroform solution just referred to and an aqueous solution (8 ml) of sodium hydroxide (200 mg, 5.0 mmol) were added dropwise while maintaining the reaction temperature below 15° C. in such a way that the additions of both of the solutions were simultaneously completed. The resulting mixture was stirred at 5° C. for one hour, followed by separation of a chloroform layer. The chloroform layer was dried over sodium sulfate and then evaporated under reduced pressure to obtain 781 mg of the intended compound as viscous light-yellowish oil (yield: 100%).

IR $\nu_{max}^{neat}$(cm$^{-1}$): 3440, 2940, 2870, 2800, 1680, 1465 1450, 1420, 1310, 1250, 1230, 1100, 750, 700.

NMR (CDCl$_3$)δ:
0.67 (3H, d, J = 7Hz, CHC$\underline{H}$$_3$)
0.80 (3H, d, J = 7Hz, CHC$\underline{H}$$_3$)

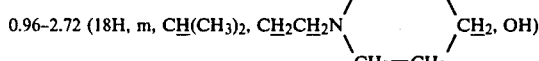

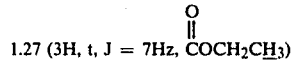

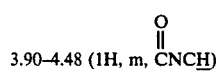

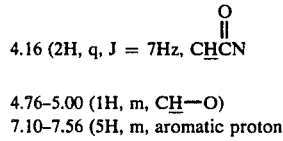

4.76–5.00 (1H, m, C$\underline{H}$—O)
7.10–7.56 (5H, m, aromatic protons)

(2)
(4RS,5SR)-4-(2-methylpropyl)-5-phenyl-3-(3-peperidinopropyl)-1,3-oxazolidine-2-one A toluene solution (12 ml) of the compound (633 mg, 1.62 mmol) obtained in item (1) of this Example was heated to about 130° C. on an oil bath to completely remove water present in the system. The bath temperature was lowered to 100° C. and aluminum isopropoxide (16 mg, 0.08 mmol) was added. The bath temperature was then held at 130° to 140° C. to remove by distillation an azeotropic mixture (9 ml) of ethanol and toluene (about one hour spent). After being cooled, the residue was added with ethyl acetate. The solution was washed first with an aqueous saturated sodium sulfate solution and then with brine. The resulting solution was dried over sodium sulfate and then evaporated under reduced pressure to obtain 558 mg of the intended compound as light-yellowish crystals (yield: 100%).

IR $\nu_{max}^{neat}$(cm$^{-1}$): 2930, 2800, 2770, 1750, 1490, 1460, 1440, 1410, 1375, 1345, 1315, 1245, 1215, 1170, 1120, 1035, 1010, 755, 695.

NMR (CDCl$_3$)δ:
0.44–0.68 (3H, m, CHC$\underline{H}$$_3$)
0.68–0.92 (3H, m, CHC$\underline{H}$$_3$)
1.00–1.26 (3H, m, CH$_2$CH(CH$_3$)$_2$)

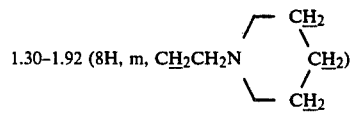

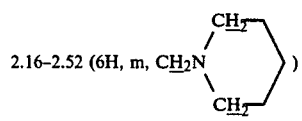

-continued

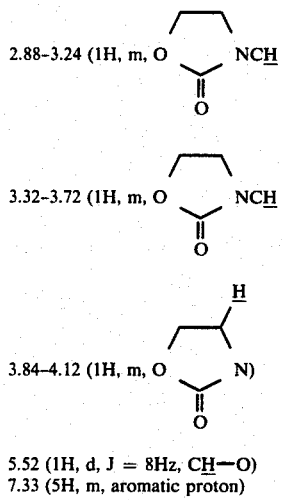

2.88-3.24 (1H, m, O NCH)

3.32-3.72 (1H, m, O NCH)

3.84-4.12 (1H, m, O N)

5.52 (1H, d, J = 8Hz, CH—O)
7.33 (5H, m, aromatic proton)

EXAMPLE 3

(4S,5R)-4-(2-methylpropyl)-5-phenyl-3-(3-piperidinopropyl)-1,3-oxazolidine-2-one fumarate A mixture of (4S,5R)-4-(2-methylpropyl)-5-phenyl-1,3-oxazolidine-2-one (10.97 g, 50 mmol), 1-(3-chloropropyl)piperidine hydrochloride (12.38 g, 62.5 mmol), anhydrous potassium carbonate powder (17.28 g, 125 mmol) and methyl ethyl ketone (100 ml) was heated under reflux with stirring for 24 hours. After completion of the reaction, the reaction mixture was cooled and insoluble matter was removed by filtration. The insoluble matter was washed with methyl ethyl ketone. The washing and filtrate were combined together and concentrated under reduce pressure. The residue was dissolved in toluene (70 ml). The toluene solution was washed three times with water (70 ml) and the toluene was then evaporated under reduced pressure. The residue was then dissolved in ethanol (50 ml), followed by addition of fumaric acid (5.80 g, 50 mmol). The resulting mixture was heated to dissolve the fumaric acid. The solution was allowed to stand overnight at room temperature. Precipitated crystals were collected by filtration, washed three times with ethanol (30 ml) and then dried to give crude crystals (19.04 g). The crude crystals were recrystallized from water (70 ml) to obtain 16.73 g of the intended compound as white crystals (yield: 73%).

m.p.: 174°-176° C. (decomposed).
$[\alpha]_D := +12.0°$ (c 1.00, MeOH).
IR $\nu_{max}^{KBr}$(cm$^{-1}$): 3560, 3450, 2950, 2640, 2350, 1740, 1725, 1690, 1635, 1540, 1450, 1405, 1240, 1200, 995, 975, 765, 745, 695.

EXAMPLE 4

Using the procedures similar to those of Examples 1 to 3, there were obtained the compounds given in Table 4.

TABLE 4

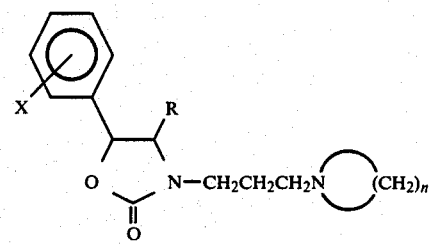

| Compound No. | R | X | n | Configuration | m.p. (°C.) | IR $\nu_{max}$ (cm$^{-1}$) |
|---|---|---|---|---|---|---|
| 1 (Ex.1) | —CH(CH₃)CH₃ | H | 5 | 4RS,5SR | 142–144 (decomposed) (Fumarate) | 2930, 2860, 2760, 1730, 1605, 1440, 1415, 1125, 1030, 755, 695. (KBr) |
| 2 | —CH(CH₃)CH₃ | H | 5 | 4RS,5RS | 157–158 (Fumarate) | 2940, 2860, 2780, 1755, 1605, 1440, 1425, 1230, 1125, 1035, 1025, 750, 695. (neat) |
| 3 (Ex. 2) | —CH₂CH(CH₃)CH₃ | H | 5 | 4RS,5SR | 150.5–151.5 (Fumarate) | 2930, 2800, 2770, 1750, 1490, 1460, 1440, 1410, 1375, 1345, 1315, 1245, 1215, 1170, 1120, 1035, 1010, 755, 695. (KBr) |
| 4 | —CH₂CH(CH₃)CH₃ | H | 5 | 4RS,5RS | 137–140 (Fumarate) | 2930, 2810, 2760, 1740, 1435, 1425, 1375, 1315, 1245, 1170, 1150, 1125, 1115, 1055, 1030, 1000, 935, 755, 750, 695. (KBr) |
| 5 (Ex. 3) | —CH₂CH(CH₃)CH₃ | H | 5 | 4S,5R $[\alpha]_D^{23} - 9.7°$ (c1.14,CHCl₃) | 174–176 (decomposed) (Fumarate) | 2920, 2860, 2790, 2760, 1750, 1460, 1440, 1405, 1360, 1245, 1200, 1160, 1110, 1030, 1000, 755, 740, 690. (neat) |

TABLE 4-continued

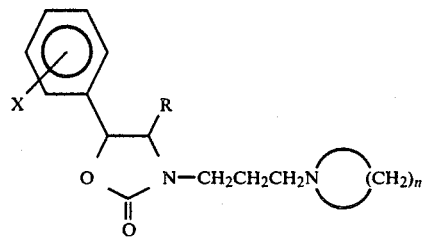

| Compound No. | R | X | n | Configuration | m.p. (°C.) | IR $\nu_{max}$ (cm$^{-1}$) |
|---|---|---|---|---|---|---|
| 6 | —CH$_2$CH(CH$_3$)CH$_3$ | H | 5 | 4R,5S $[\alpha]_D^{23}$ + 9.7° (cl.12,CHCl$_3$) | 47–49 174–176 (decomposed) (Fumarate) | 2920, 2860, 2790, 2760, 1750, 1460, 1440, 1405, 1360, 1245, 1200, 1160, 1110, 1030, 1000, 755, 740, 690. (KBr) |
| 7 | —CH$_2$CH(CH$_3$)CH$_3$ | H | 5 | 4S,5S $[\alpha]_D^{23}$ + 10.3° (cl.13,CHCl$_3$) | 160–161 (Fumarate) | 2930, 2760, 1750, 1460, 1440, 1410, 1370, 1340, 1310, 1245, 1210, 1165, 1130, 1115, 1055, 1030, 1005, 750, 690. (neat) |
| 8 | —CH$_2$CH(CH$_3$)CH$_3$ | H | 5 | 4R,5R $[\alpha]_D^{23}$ − 10.3° (cl.13,CHCl$_3$) | 160–162 (Fumarate) | 2930, 2760, 1750, 1460, 1440, 1410, 1370, 1340, 1310, 1245, 1210, 1165, 1130, 1115, 1055, 1030, 1005, 750, 690. (neat) |
| 10 | —CH(CH$_3$)CH$_3$ | H | 4 | 4RS,5RS | 145–147 (Fumarate) | 2960, 2880, 2790, 1750, 1445, 1420, 1230, 1030, 755, 700. (neat) |
| 13 | —CH$_2$CH(CH$_3$)CH$_3$ | H | 4 | 4RS,5SR | 169–170 (Fumarate) | 2960, 2880, 2790, 1750, 1605, 1450, 1410, 1145, 1030, 1010, 755, 700. (neat) |
| 14 | —CH$_2$CH(CH$_3$)CH$_3$ | H | 4 | 4RS,5RS | 147–148 (Fumarate) | 2960, 2880, 2790, 1750, 1605, 1450, 1415, 1245, 1145, 1040, 1010, 760, 695. (neat) |
| 17 | —CH$_2$CH(CH$_3$)CH$_3$ | H | 6 | 4S,5R $[\alpha]_D$ − 10.7° (cl.15,CHCl$_3$) | 171–173 (decomposed) (Fumarate) | 2920, 2860, 2810, 1755, 1460, 1445, 1410, 1360, 1025, 1005, 760, 695. (neat) |
| 21 | —CH$_2$CH(CH$_3$)CH$_3$ | 2-CH$_3$ | 5 | 4RS,5SR | 152–153 (Fumarate) | 2950, 2880, 2820, 2780, 1760, 1445, 1420, 1235, 1220, 1130, 1040, 1010, 755 (neat) |
| 23 | —CH$_2$CH(CH$_3$)CH$_3$ | 3-CH$_3$ | 5 | 4RS,5SR | 142–145 (decomposed) (Fumarate) | 2930, 2860, 2760, 1750, 1605, 1440, 1405, 1120, 1075, 750. |
| 24 | —CH$_2$CH(CH$_3$)CH$_3$ | 3-CH$_3$ | 5 | 4RS,5RS | — | 2920, 2860, 2760, 1750, 1435, 1405, 1370, 1240, 1115, 1030, 775, 750, 690. (neat) |
| 25 | —CH$_2$CH(CH$_3$)CH$_3$ | 4-CH$_3$ | 5 | 4RS,5SR | 132–134 (Fumarate) | 2940, 2880, 2780, 1760, 1445, 1415, 1125, 1040, 1015, 815, 760. (neat) |
| 26 | —CH$_2$CH(CH$_3$)CH$_3$ | 4-CH$_3$ | 5 | 4RS,5RS | — | 2940, 2870, 2770, 1755, 1605, 1440, 1410, 1250, 1120, 1035, 1010, 810, 755. (neat) |

TABLE 4-continued

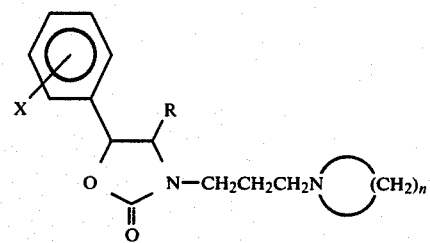

| Compound No. | R | X | n | Configuration | m.p. (°C.) | IR $\nu_{max}$ (cm$^{-1}$) |
|---|---|---|---|---|---|---|
| 27 | —CH$_2$CH(CH$_3$)$_2$ | 4-OCH$_3$ | 5 | 4RS,5SR | 127.5–129.5 (Fumarate) | 2930, 2760, 1750, 1610, 1510, 1435, 1405, 1250, 1170, 1030, 825, 750. (neat) |
| 29 | —CH$_2$CH(CH$_3$)$_2$ | 4-F | 5 | 4RS,5SR | 140–141 (decomposed) (Fumarate) | 2930, 2850, 2750, 1720, 1605, 1505, 1445, 1410, 1360, 1225, 1150, 1120, 1030, 990, 845, 810, 755. (KBr) |
| 30 | —CH$_2$CH(CH$_3$)$_2$ | 4-F | 5 | 4RS,5RS | 123–125 (Fumarate) | 2930, 2870, 2800, 2770, 1750, 1605, 1510, 1470, 1445, 1415, 1225, 1155, 1120, 1030, 1005, 830, 760. (neat) |
| 31 | —CH$_2$CH(CH$_3$)$_2$ | 4-Cl | 5 | 4RS,5SR | 141–142 (decomposed) (Fumarate) | 2940, 2860, 2820, 2770, 1735, 1605, 1495, 1450, 1425, 1370, 1350, 1250, 1235, 1215, 1125, 1090, 1025, 1010, 995, 945, 820, 770. (KBr) |
| 32 | —CH$_2$CH(CH$_3$)$_2$ | 4-Cl | 5 | 4RS,5RS | — | 2940, 2870, 2850, 2810, 2770, 1750, 1600, 1490, 1465, 1440, 1410, 1250, 1120, 1090, 1030, 1005, 820, 750. (neat) |
| 33 | —(CH$_2$)$_2$CH$_3$ | H | 5 | 4RS,5RS | 198–201 (decomposed) (Oxalate) | 2920, 2840, 2760, 1740, 1600, 1440, 1415, 1240, 1120, 1030, 1000, 755, 695. (neat) |
| 34 | —(CH$_2$)$_2$CH$_3$ | H | 5 | 4RS,5SR | 126–128 (Fumarate) | 2930, 2870, 2770, 1740, 1440, 1410, 1010, 770, 705. (KBr) |
| 35 | —(CH$_2$)$_3$CH$_3$ | H | 5 | 4RS,5RS | 98–100 (Fumarate) | 2940, 2860, 2770, 1750, 1605, 1450, 1415, 1230, 1120, 1035, 1000, 755, 695. (neat) |
| 36 | —(CH$_2$)$_3$CH$_3$ | H | 5 | 4RS,5SR | 118–120 (Fumarate) | 2930, 2860, 2760, 1750, 1605, 1450, 1410, 1120, 1030, 1010, 755, 695. (neat) |
| 37 | —(CH$_2$)$_4$CH$_3$ | H | 5 | 4RS,5RS | 134–136 (Oxalate) | 2940, 2860, 2800, 2770, 1755, 1450, 1415, 1375, 1240, 1230, 1120, 1035, 1000, 755, 695. (neat) |
| 38 | —(CH$_2$)$_4$CH$_3$ | H | 5 | 4RS,5SR | 113–115 (Fumarate) | 2930, 2860, 2800, 2760, 1750, 1445, 1410, 1245, 1225, 1120, 1030, 1010, 755, 695. (neat) |
| 39 | —(CH$_2$)$_2$CH(CH$_3$)$_2$ | H | 5 | 4RS,5RS | 125–126 (Maleate) | 2940, 2870, 2780, 1755, 1610, 1450, 1420, 1240, 1130, 1040, 1010, 760, 700. (neat) |
| 40 | —(CH$_2$)$_2$CH(CH$_3$)$_2$ | H | 5 | 4RS,5SR | 138–139 (Fumarate) | 2920, 2850, 2740, 1740, 1600, 1440, 1405, 1115, 1025, 1005, 745, 690. (neat) |
| 41 | —(CH$_2$)$_5$CH$_3$ | H | 5 | 4RS,5RS | 92–94 (Fumarate) | 2920, 2850, 2770, 1750, 1600, 1450, 1410, 1230, 1120, 1030, 1010, 755, 695. (neat) |
| 42 | —(CH$_2$)$_5$CH$_3$ | H | 5 | 4RS,5SR | 121–123 (Fumarate) | 2930, 2850, 2770, 1750, 1605, 1450, 1410, 1120, 1035, 760, 700. (neat) |

REFERENCE EXAMPLE 1

2-(1,3-dioxo-2-azaindane-2-yl)-4-methyl-1-phenylpentane-1-one

Thionyl chloride (34.8 ml, 480 mmol) was added to a mixture of 2-(1,3-dioxo-2-azaindane-2-yl)-4-methylpentanoic acid (83.61 g, 320 mmol) and benzene (320 ml). The resulting mixture was heated under reflux for 2 hours. The solvent and excess thionyl chloride were removed by distillation under reduced pressure, followed by addition of benzene (320 ml). The benzene was removed and fresh benzene (480 ml) was added to form a solution. Anhydrous aluminum chloride (106.7 g, 800 mmol) was added immediately to the solution and the mixture was stirred at room temperature for 3 hours. The reaction mixture was poured into ice water (700 ml). The aqueous layer was extracted with benzene (200 ml). After being washed first with water and then with an aqueous sodium bicarbonate solution and with brine, the combined organic layer was dried over sodium sulfate and then evaporated under reduced pressure. The residue was treated with ethanol to obtain crystals. The crystals were dissolved with heating in ethanol (80 ml) and added with hexane (160 ml). Precipitated crystals were collected by filtration and washed first with a 1:2 mixed solution (240 ml) of ethanol and hexane and then with hexane. The crystals were dried in air to obtain 74.6 g of the intended compound as white crystals (yield: 73%).

REFERENCE EXAMPLE 2

(1RS,2SR)-2-(1,3-dioxo-2-azaindane-2-yl)-4-methyl-1-phenylpentane-1-ol- and
(1RS,2RS)-2-(1,3-dioxo-2-azaindane-2-yl)-4-methyl-1-phenylpentane-1-ol Sodium cyanoborohydride (177 g, 2.82 mol) was added over 3 hours to a solution of the compound (141.4 g, 440 mmol) obtained in Reference Example 1 in chloroform (660 ml) and acetic acid (440 ml) while maintaining the reaction temperature below 30° C. The resulting mixture was stirred at room temperature for further 3 hours and added with chloroform (1 liter) and with water (1.4 liters). The organic layer was separated and washed twice with water, once with an aqueous sodium bicarbonate solution and once with brine. After being dried over sodium sulfate, the organic layer was evaporated under reduced pressure to provide white crystals (142 g). The crystals were then charged on silica gel column chromatography (silica gel: 2.8 kg, solvent: benzene) to obtain first 94.3 g of the (1RS, 2SR) isomer as white crystals (yield: 66%) and then 48.4 g of the (1RS,2RS) isomer as white crystals (yield: 34%).

REFERENCE EXAMPLE 3

(1RS,2RS)-2-(1,3-dioxo-2-azaindane-2-yl)-4-methyl-1-phenylpentane-1-ol

Aluminum isopropoxide (125.6 g, 615 mmcl) was added to a suspension of 2-(1,3-dioxo-2-azaindane-2-yl)-4-methyl-1-phenylpentane-1-one (72.3 g, 225 mmcl) in isopropanol (1,000 ml). The mixture was heated under reflux for 6.5 hours. The isopropanol was removed by distillation under reduced pressure and the residue was added with ethyl acetate (800 ml) and further with an aqueous solution of sodium sulfate. The resulting organic layer was decanted and the residue was washed twice with ethyl acetate (200 ml). The combined organic layer was washed with brine. The organic solution was dried and the solvent was removed by distillation under reduced pressure. The residue was recrystallized twice from benzene to obtain 29.3 g of the intended compound as white crystals (yield: 40%).

REFERENCE EXAMPLE 4

(1RS,2SR)-2-amino-4-methyl-1-phenylpentane-1-ol (1RS,2SR)-2-(1,3-Dioxo-2-azaindane-2-yl)-4-methyl-1-phenylpentane-1-ol (80.0 g, 247 mmol) was dissolved with heating (50° C.) in ethanol (800 ml), followed by addition of a mixture of 85% hydrazine hydrate (19.0 ml) in ethanol (200 ml). The resulting mixture was heated under reflux for 3 hours and, after cooled, ice-cooled and added with 4N hydrochloric acid (700 ml). The mixture was stirred at room temperature for 30 minutes. Insoluble matter was removed by filtration through cellite and then washed with 4N hydrochloric acid (140 ml). The washing was added to the filtrate and the solution was condensed under reduced pressure to remove the ethanol. A 6N sodium hydroxide solution (570 ml) was added with ice-cooling and the mixture was extracted three times with chloroform. After being dried over sodium sulfate, the organic layer was evaporated to obtain 43.2 g of the intended compound as white crystals (yield: 91%).

REFERENCE EXAMPLE 5

4-methyl-1-(4-methylphenyl)-2-(1,3-dioxo-2-azaindane-2-yl)pentane-1-one

2-Bromo-4-methyl-1-(4-methylphenyl)pentane-1-one (13.5 g, 50 mmol) and potassium phthalimide (9.26 g, 50 mmol) were thoroughly mixed and heated at 160° C. for 2 hours. After being cooled, the reaction mixture was added with ethyl acetate (100 ml) and with water (50 ml). The resulting organic layer was separated and washed with brine. The organic solution was then dried over sodium sulfate and evaporated under reduced pressure. The residue was crystallized by treatment with hexane and the resulting crystals were recrystallized from hexane to obtain 12.2 g of the intended compound as white crystals (yield: 73%).

REFERENCE EXAMPLE 6

(1RS,2RS)-2-amino-1-phenylheptane-1-ol

Acetic anhydride (10 ml) was added to (1RS,2SR)-2-amino-1-phenylheptane-1-ol (4.15 g, 20 mmol) and the mixture was heated at 70° C. for 10 minutes. After being cooled, the reaction mixture was poured into water (100 ml) to which chloroform was added, followed by gradual addition of an aqueous sodium hydroxide solution. The solution thus basified was extracted with chloroform and the extract was dried. The solvent was removed by distillation under reduced pressure to obtian a colorless oil. The oil was ice-cooled, followed by addition of thionyl chloride (20 ml). The mixture was stirred at room temperature for 20 minutes. Water (30 ml) was added in limited amounts with caution and the mixture was heated under reflux for 2 hours. The mixture was cooled and then added with water. Subsequent to washing of the mixture with ether, the resulting aqueous layer was separated and basified with an aqueous sodium hydroxide solution. The mixture was extracted three times with chloroform and dried. The organic solution was evaporated under reduced pressure to give white crystals. The crystals were recrystallized from hexane to obtain 2.73 g of the intended compound as white crystals (yield: 66%).

REFERENCE EXAMPLE 7

(1RS,2SR)-2-amino-1-(4-methoxyphenyl)-4-methylpentane-1-ol

2-Hydroxyimino-1-(4-methoxyphenyl)-4-methyl-pentane-1-one (8.72 g; 37.1 mmol) was dissolved in acetic acid (88 ml). The solution was added with 5% palladium-charcoal (0.87 g) and the reactant was catalytically hydrogenated at normal pressure and at 80° C. until hydrogen was absorbed in a molar amount of three times that of the reactant. After removal of the catalyst by filtration, the acetic acid was removed under reduced pressure. The residue was dissolved in 1N hydrochloric acid (80 ml). The solution was washed twice with ether (30 ml) and the aqueous layer was basified with a 20% aqueous solution of sodium hydroxide. The aqueous layer thus treated was extracted three times with chloroform and the extracts were combined together and then washed once with brine. The resulting extract was dried over sodium sulfate and the solvent was removed by distillation under reduced pressure to give light-yellowish crystals (6.80 g). The crystals were recrystallized from benzene and hexane to obtain 5.24 g of the intended compound as white crystals (yield: 63%).

REFERENCE EXAMPLE 8

(1RS,2SR)-4-methyl-1-phenyl-2-(3-piperidinopropylamino)pentane-1-ol dihydrochloride A mixture of (1RS,2SR)-2-amino-4-methyl-1-phenylpentane-1-ol (40.6 g, 210 mmol) and 1-(3-chloropropyl)-piperidine (34.0 g, 210 mmol) was melted together at 50° to 70° C. in a nitrogen atmosphere. The mixture was then heated on an oil bath of 110° to 120° C. for 3 hours. After being cooled, the reaction mixture was dissolved with heating in ethanol (750 ml), followed by addition of concentrated hydrochloric acid (17 ml). The mixture was cooled and precipitated crystals were collected by filtration. The crystals were agian suspended in ethanol (1,200 ml) and heated under reflux for one hour. The mixture was cooled and the resulting crystals were collected by filtration, washed and then dried to obtain 58.8 g of the intended compound as white crystals [yield: 72%, m.p.: 268°–270° C. (decomposed)].

Amino alcohols useful as starting compounds for the compounds of this invention were synthesized with the combined use of the processes illustrated in the Reference Examples (Process A: Reference Examples 1, 2, 4 and 8, Process B; Reference Examples 6 and 8, Process C; Reference Examples 7 and 8, Process D: Reference Examples 5, 3, 4 and 8 and Process E: Reference Examples 5, 2, 4 and 8). The starting compounds thus obtained are given in Table 5.

TABLE 5

General structure: X-phenyl-CH(OH)-CH(R)-NHCH$_2$CH$_2$CH$_2$N(CH$_2$)$_n$ · 2HCl (piperidine ring)

| R | X | n | Configuration | m.p. (°C.) | Process |
|---|---|---|---|---|---|
| —CH(CH$_3$)$_2$ | H | 5 | 1RS,2SR | 210–212 (decomposed) | A |
| —CH(CH$_3$)$_2$ | H | 5 | 1RS,2RS | 238–240 (decomposed) | A |
| —CH$_2$CH(CH$_3$)$_2$ | H | 5 | 1RS,2SR | 268–270 (decomposed) | A |
| —CH$_2$CH(CH$_3$)$_2$ | H | 5 | 1RS,2RS | 244–246 (decomposed) | A |
| —CH$_2$CH(CH$_3$)$_2$ | H | 5 | 1R,2S; [α]$_D$ −24.9° (c 0.62, MeOH) | 266–267 (decomposed) | A |
| —CH$_2$CH(CH$_3$)$_2$ | H | 5 | 1S,2R; [α]$_D$ +25.3° (c 0.60, MeOH) | 266–267 (decomposed) | A |
| —CH$_2$CH(CH$_3$)$_2$ | H | 5 | 1S,2S; [α]$_D$ +24.3° (c 0.60, MeOH) | 234–236 (decomposed) | A |
| —CH$_2$CH(CH$_3$)$_2$ | H | 5 | 1R,2R; [α]$_D$ −24.3° (c 0.60, MeOH) | 230–232 (decomposed) | A |

TABLE 5-continued $$\text{X}\underset{\text{R}}{\overset{\text{OH}}{\text{C}_6\text{H}_4\text{-CH-CH-}}}\text{NHCH}_2\text{CH}_2\text{N}\diagdown(\text{CH}_2)_n\cdot 2\text{HCl}$$

| R | X | n | Configuration | m.p. (°C.) | Process |
|---|---|---|---|---|---|
| —CH(CH₃)₂ | H | 4 | 1RS,2RS | 208.5–210.5 (decomposed) | A |
| —CH₂CH(CH₃)₂ | H | 4 | 1RS,2SR | 240–241 (decomposed) | A |
| —CH₂CH(CH₃)₂ | H | 4 | 1RS,2RS | 226.5–228.5 (decomposed) | A |
| —CH₂CH(CH₃)₂ | 2-CH₃ | 5 | 1RS,2SR | 236–238 (decomposed) | C |
| —CH₂CH(CH₃)₂ | 3-CH₃ | 5 | 1RS,2SR | 255–256 (decomposed) | C |
| —CH₂CH(CH₃)₂ | 3-CH₃ | 5 | 1RS,2RS | 240–243 (decomposed) | B |
| —CH₂CH(CH₃)₂ | 4-CH₃ | 5 | 1RS,2SR | 257–259 (decomposed) | C |
| —CH₂CH(CH₃)₂ | 4-CH₃ | 5 | 1RS,2RS | 243–246 (decomposed) | D |
| —CH₂CH(CH₃)₂ | 4-OCH₃ | 5 | 1RS,2SR | 250–251 (decomposed) | C |
| —CH₂CH(CH₃)₂ | 4-F | 5 | 1RS,2SR | 275–276 (decomposed) | C |
| —CH₂CH(CH₃)₂ | 4-F | 5 | 1RS,2RS | 250–251 (decomposed) | D |
| —CH₂CH(CH₃)₂ | 4-Cl | 5 | 1RS,2SR | 278–279 (decomposed) | E |
| —CH₂CH(CH₃)₂ | 4-Cl | 5 | 1RS,2RS | 252–253 (decomposed) | E |

TABLE 5-continued $$X-\text{C}_6\text{H}_4-\text{CH(OH)}-\text{CHR}-\text{NHCH}_2\text{CH}_2\text{CH}_2\text{N}(\text{CH}_2)_n \cdot 2\text{HCl}$$

| R | X | n | Configuration | m.p. (°C.) | Process |
|---|---|---|---|---|---|
| —CH$_2$CH(CH$_3$)CH$_3$ | H | 6 | 1R,2S; [α]$_D$ −19.3° (c 0.60, MeOH) | 238–240 (decomposed) | A |
| —(CH$_2$)$_5$CH$_3$ | H | 5 | 1RS,2RS | 231–234 (decomposed) | A |
| —(CH$_2$)$_2$CH$_3$ | H | 5 | 1RS,2SR | 259–261 (decomposed) | A |
| —(CH$_2$)$_2$CH$_3$ | H | 5 | 1RS,2RS | 223–227 (decomposed) | A |
| —(CH$_2$)$_3$CH$_3$ | H | 5 | 1RS,2SR | 257–258 (decomposed) | A |
| —(CH$_2$)$_3$CH$_3$ | H | 5 | 1RS,2RS | 232–235 (decomposed) | A |
| —(CH$_2$)$_4$CH$_3$ | H | 5 | 1RS,2SR | 261–262 (decomposed) | A |
| —(CH$_2$)$_4$CH$_3$ | H | 5 | 1RS,2RS | 238–241 (decomposed) | A |
| —(CH$_2$)$_2$CH(CH$_3$)$_2$ | H | 5 | 1RS,2SR | 266–267 (decomposed) | A |
| —(CH$_2$)$_2$CH(CH$_3$)$_2$ | H | 5 | 1RS,2RS | 250–251 (decomposed) | A |
| —(CH$_2$)$_5$CH$_3$ | H | 5 | 1RS,2SR | 253–255 (decomposed) | A |

REFERENCE EXAMPLE 9

(4S,5R)-4-(2-methylpropyl)-5-phenyl-1,3-oxazolidine-2-one (1R,2S)-2-Amino-4-methyl-1-phenylpentane-1-ol (96.64 g, 0.5 mmol) was dissolved in chloroform (800 ml), followed by addition of water (400 ml), and the mixture was ice-cooled. Ethyl chlorocarbonate (47.5 ml) was added dropwise with stirring at a temperature below 10° C. Additional ethyl chlorocarbonate (47.5 ml) and a 7.5N aqueous solution of sodium hydroxide (150 ml) were added dropwise at the same temperature as referred to above. These dropwise additions were simultaneosuly completed. The resulting mixture was continuously stirred at the same temperature for further 30 minutes. An organic layer was separated and an aqueous layer was extracted with chloroform (80 ml). The combined organic layer was dried over sodium sulfate and then evaporated under reduced pressure. The residue was dissolved in toluene (1.5 liters) and 200 ml of the toluene was then removed by distillation. Aluminum isopropoxide (2.0 g) was added and the mixture was heated under reflux for one hour. 800 ml of the toluene was removed by distillation to remove by-produced alcohols. n-Hexane (600 ml) was added with stirring to the residue and the solution was allowed to stand overnight. Precipitated white crystals were collected by filtration and washed twice with a 1:1 mixed solvent (300 ml) of toluene and n-hexane and then once with n-hexane (300 ml). The crystals were dried to obtain 104.5 g of the intended compound (yield: 95%).

m.p.: 163°–164° C.

[α]$_D^{25}$: −137.4° (c 1.016,CHCl$_3$).

IR ν$_{max}^{KBr}$(cm$^{-1}$): 3260, 2960, 2945, 1750, 1735, 1350 1250, 1220, 1050, 995, 975, 950, 740 725, 695.

NMR (CDCl$_3$)δ:

0.79 (3H, d, J = 6Hz, CH$_3$)
0.81 (3H, d, J = 6Hz, CH$_3$)
0.90–1.70 (3H, m, CH$_2$CH(CH$_3$)$_2$)

3.96–4.28 (1H, CNHCH, O=)

5.70 (1H, d, J = 8Hz, PhCH)
6.87 (1H, broad s, NH)
7.32 (5H, m, aromatic proton)

Having thus described this invention, it will be apparent to those versed in the art that various changes or modifications may be made thereto without departing from the spirit or scope of the invention set out in the appended claims.

What is claimed is:

1. A 1,3-oxazolidine-2-one represented by the following formula:

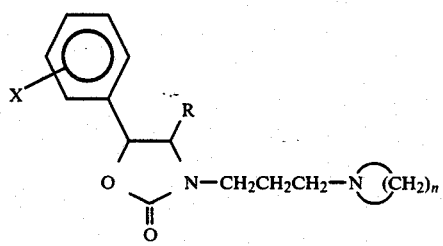

wherein R is a straight or branched alkyl group having 3 to 8 carbon atoms, X is a hydrogen or halogen atom or a lower alkyl or lower alkoxy group and n is an integer of 4 to 6, or an acid addition salt thereof.

2. The 1,3-oxazolidine-2-one claimed in claim 1 represented by the following formula:
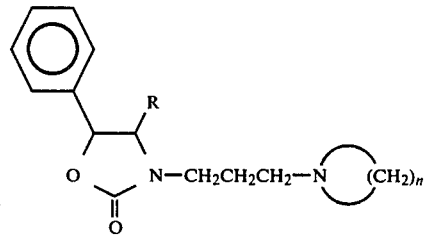
wherein R is an isopropyl or isobutyl group, and n is an integer of 5 or 6.
3. (4S, 5R)-4-(2-Methylpropyl)-5-phenyl-3-(3-piperidinopropyl)-1,3-oxazolidine-2-one.
4. (4S, 5R)-4-(2-Methylpropyl)-3-[3-(perhydroazepine-1-yl)propyl]-5-phenyl-1,3-oxazolidine-2-one.
* * * * *